US006054460A

United States Patent [19]
Arnold et al.

[11] Patent Number: 6,054,460
[45] Date of Patent: Apr. 25, 2000

[54] ANTICONVULSIVE AND ANTIALLERGIC/ANTIASTHMATIC PYRAZOLO-[3,4-D] PYRIMIDINES, AND PROCESS FOR PREPARING

[75] Inventors: Thomas Arnold, Radebeul; Hans-Joachim Lankau, Weinböhla; Manfred Menzer; Angelika Rostock, both of Dresden; Christine Tober, Weinböhla; Klaus Unverferth, Dresden, all of Germany

[73] Assignee: Arzneimittelwerk Dresden GmbH, Germany

[21] Appl. No.: 09/333,709

[22] Filed: Jun. 15, 1999

[30] Foreign Application Priority Data

Jun. 22, 1998 [DE] Germany .................. 192 27 679

[51] Int. Cl.[7] .................. A61K 31/519; C07D 487/04
[52] U.S. Cl. ............................ 514/258; 544/262
[58] Field of Search .................. 544/262; 514/258

[56] References Cited

FOREIGN PATENT DOCUMENTS 196 49 460
   A1   5/1998   Germany .

WO 88/00192  1/1988  WIPO .

OTHER PUBLICATIONS

Gatta, F. et al., "Pyrazolo [3,4–D]pyrimidines Related to Lonidamine", J. Heterocyclic Chem., vol. 26, pp 613, 1989.

El Hedi Jellali, M. et al., "Acylation and alkylation of 4–aminopyrazolo [3,4–d] Pyrimidine", Tetrahedron, vol. 31, pp 587, 1975.

Eisenacher, Th. et al., "Ueber Neue Pyrazolverbindungen: 6.Mitteilung: Pyrazolo [3,4–d] pyrimidinylessigsaurederivate", Pharmazie Bd. 46, Nr. 10, 1991.

Eisenaecher et al. New pyrazole compounds. Pharmazie 46(10), 747–8, 1991.

*Primary Examiner*—Mukund J. Shah
*Assistant Examiner*—V Balasubramanian
*Attorney, Agent, or Firm*—Schweitzer Cornman Gross & Bondell LLP

[57] ABSTRACT

The invention relates to pyrazolo[3,4d]pyrimidin-4(5H)-ones and pyrazolo[3,4-d]pyrimidine-4(5H)-thiones and their tautomers and pharmaceutically acceptable salts, which contain a benzyl radical in the 2-position, processes for their preparation and their use as medicaments, in particular for the treatment of epilepsies of various forms and of allergic/asthmatic diseases.

9 Claims, No Drawings

ANTICONVULSIVE AND ANTIALLERGIC/ANTIASTHMATIC PYRAZOLO-[3,4-D]PYRIMIDINES, AND PROCESS FOR PREPARING

FIELD OF INVENTION

The invention relates to pyrazolo[3,4-d]pyrimidin-4(5H)-ones and pyrazolo[3,4-d]pyrimidine-4(5H)-thiones and their tautomers which contain a benzyl group in the 2-position, processes for their preparation and their use as medicaments, in particular for the treatment both of epilepsies of various forms and of allergic diseases such as bronchial asthma, allergic rhinoconjunctivitis or atopic dermatitis.

BACKGROUND

The adenosine receptor is of importance as a target for influencing disregulations in various organ systems (e.g. the central nervous system, airways, etc.). On account of the structural similarities to adenine, pyrazolo[3,4-d]pyrimidines are pharmacologically interesting compounds.

2-Benzyl-substituted pyrazolo[3,4-d]pyrimidine-4(5H)-thiones and tautomers are not known compounds. Pyrazolo[3,4-d]pyrimidin-4(5H)-ones and tautomers with a substituted benzyl radical in the 2-position are likewise not known.

So far only 2-benzylpyrazolo[3,4-d]pyrimidin-4(5H)-one has been described [R. Böhm, Pharmazie 1986, 41, 430; Th. Eisenächer, R. Pech, R. Böhm, Pharmazie 1991, 46, 747]. This compound is obtained by cyclization of ethyl 3-amino-1-benzylpyrazole-4-carboxylate with formamide. 2-Benzyl-substituted 3-amino-pyrazole-4-carboxylic acid esters can be obtained by benzylation of 3-amino-pyrazole-4-carboxylic acid esters [S. Senda, K. Hirota, G.-N. Yang, Chem. Pharm. Bull. 1972, 20(2) 391].

No actual pharmacological action has been mentioned or suggested for 2-benzyl-pyrazolo[3,4-d]pyrimidin-4(5H)-one.

Known anticonvulsants produce undesired side effects, such as neurotoxicity and idiosyncrasies, occur and on the other hand these anticonvulsants are also not active in certain forms of epilepsy.

Various forms of allergic/asthmatic disorders, such as bronchial asthma, can likewise be inadequately treated by these drugs.

DESCRIPTION OF THE INVENTION

It is an object of the present invention to provide compounds with favorable pharmacological properties, and which can be employed as drugs, particularly for the treatment of epilepsies and various allergic/asthmatic diseases.

The new compounds of the present invention are 2-ar(alkyl)pyrazolo[3,4-d]pyrimidin-4(5H)-ones and 2-ar(alkyl)pyrazolo[3,4-d]pyrimidine-4(5H)-thiones of the Formula (1)

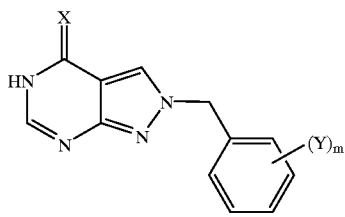

(1)

their tautomers, and their pharmaceutically acceptable salts, wherein
X is oxygen and sulfur,
Y is halogen, $C_{1-4}$-alkyl, $C_{1-4}$-alkoxy, trifluoromethyl or trifluoromethoxy.
Examples of compounds of Formula (1) include
and m is 1 or 2
2-(2-fluorobenzyl)pyrazolo[3,4-d]pyrimidin-4(5H)-one,
2-(2-chlorobenzyl)pyrazolo[3,4-d]pyrimidin-4(5H)-one,
2-(2-bromobenzyl)pyrazolo[3,4-d]pyrimidin-4(5H)-one,
2-(2-iodobenzyl)pyrazolo[3,4-d]pyrimidin-4(5H)-one,
2-(2-trifluoromethylbenzyl)pyrazolo[3,4-d]pyrimidin-4(5H)-one,
2-(2-methylbenzyl)pyrazolo[3,4-d]pyrimidin-4(5H)-one,
2-(3-trifluoromethylbenzyl)pyrazolo[3,4-d]pyrimidin-4(5H)-one,
2-(2,6-difluorobenzyl)pyrazolo[3,4-d]pyrimidin-4(5H)-one,
2-(2-chloro-6-fluorobenzyl)pyrazolo[3,4-d]pyrimidin-4(5H)-one,
2-(2,6-dichlorobenzyl)pyrazolo[3,4-d]pyrimidin-4(5H)-one,
2-(2,4-dichlorobenzyl)pyrazolo[3,4-d]pyrimidin-4(5H)-one,
2-(4-methoxybenzyl)pyrazolo[3,4-d]pyrimidin-4(5H)-one,
2-(2-chloro-4,5-methylenedioxybenzyl)pyrazolo[3,4-d]pyrimidin-4(5H)-one,
2-(2-chlorobenzyl)pyrazolo[3,4-d]pyrimidine-4(5H)-thione,
2-(2-bromobenzyl)pyrazolo[3,4-d]pyrimidine-4(5H)-thione,
2-(2-iodobenzyl)pyrazolo[3,4-d]pyrimidine-4(5H)-thione,
2-(2-trifluoromethylbenzyl)pyrazolo[3,4-d]pyrimidine-4(5H)-thione, and
2-(2,6-difluorobenzyl)pyrazolo[3,4-d]pyrimidine-4(5H)-thione.

Compounds of Formula (1) and their tautomers where X is oxygen, can be prepared by cyclizing 3-aminopyrazole-4-carboxylic acid esters, or 3-aminopyrazole-4-carboxamides of Formula (2)

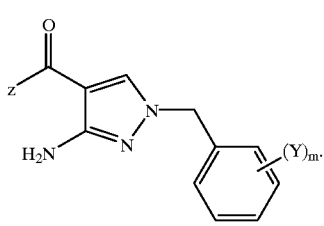

(2)

wherein
Z is hydroxyl, alkoxy or amino,
Y is halogen, $C_{1-4}$-alkyl, $C_{1-4}$-alkoxy, trifluoromethyl, or trifluoromethoxy,
and m is 1 or 2 in formamide at a temperature between from about 100° C. to about 180° C.

Compounds of Formula (1) and of their tautomers where X is sulfur, can be prepared by the substitution by sulfur of compounds of Formula (1) and their tautomers where X is oxygen, by phosphorus pentasufide or 2,4-bis(4-methoxyphenyl)-1,3-dithia-2,4-diphosphetane-2,4-disulfide.

Compounds of Formula (2) are prepared from 3-aminopyrazole-4-carboxylic acid derivatives. The compounds of Formula (2) are obtained by alkylation under phase-transfer conditions using a suitably substituted benzyl halide.

The compounds of the present invention or their pharmaceutically acceptable salts are suitable for the production of pharmaceutical compositions. The pharmaceutical compositions or drugs so made can contain one or more of the compounds of the present invention. One or more conventional pharmaceutical excipients and auxiliaries and optionally diluents can be used for the production of the pharmaceutical preparations. The pharmaceuticals can be suitably administered, for example, parenterally (e.g. intravenously, intramuscularly, subcutaneously), topically (intranasally, by inhalation), or orally.

Various forms of administration of the drugs can be prepared by suitable processes which are generally known and customary in pharmaceutical practice.

The compounds of the present invention have strong anticonvulsive or antiallergic/antiasthmatic activity.

1. Anticonvulsive Activity

The compounds of the present invention were tested in vivo for their anticonvulsive action as shown in Table 1, after i.p. administration to mice or p.o. to rats, according to the international conventional standard as described Pharmac. Week-blad, Sc. Ed. 14, 132 (1992) and Antiepileptic Drugs, Third Ed., Raven Press, New York 1989.

Analogous results were obtained for the orally administered tests. For example, for the compound 2 (2-(2-chlorobenzyl)pyrazolo[3,4-d]pyrimidin-4(5H)-one) in the rat, the ED50 (p.o.) was determined in maximal electroshock to be 32 mg/kg and the NT50 was determined to be >250 mg/kg for the neurotoxicity. Compound 15 (2-(2-chlorobenzyl)pyrazolo[3,4-d]pyrimidine-4(5H)-thione) is likewise strongly anticonvulsive together with great therapeutic breadth (ED50 (rat p.o.)=12 mg/kg, NT50>460 mg/kg).

TABLE 1

Anticonvulsive action of selected pyrazolo[3,4-d]pyrimidines

| Example[1] | Log P[2] | Test[3] | Dose[4] | Action[5] |
|---|---|---|---|---|
| | 0.2 | MES | 30 | 100 |
| 1 | | PTZ | 100 | 100 |
| | 1.01 | MES | 100 | 100 |
| 2 | | PTZ | 100 | 60 |
| | 0.56 | MES | 100 | 100 |
| 3 | | PTZ | 300 | 80 |
| | 0.74 | MES | 300 | 100 |
| 4 | | PTZ | 300 | — |
| | 1.08 | MES | 30 | 100 |
| 5 | | PTZ | 30 | 20 |
| | 0.75 | MES | 30 | 100 |
| 6 | | PTZ | 100 | 20 |
| | 1.00 | MES | 30 | 100 |
| 7 | | PTZ | 100 | 60 |
| | 0.18 | MES | 30 | 100 |
| 8 | | PTZ | 30 | 40 |
| | 0.93 | MES | 30 | 100 |

TABLE 1-continued

Anticonvulsive action of selected pyrazolo[3,4-d]pyrimidines

| Example[1] | Log P[2] | Test[3] | Dose[4] | Action[5] |
|---|---|---|---|---|
| 9 | | PTZ | 300 | — |
| | 1.16 | MES | 100 | 60 |
| 10 | | PTZ | 300 | — |
| | 1.68 | MES | 100 | 100 |
| 11 | | PTZ | 100 | 20 |
| | 0.62 | MES | 100 | 15 |
| 12 | | PTZ | 300 | 40 |
| | 1.21 | MES | 100 | 30 |
| 13 | | PTZ | 300 | — |
| | 1.54 | MES | 100 | 100 |
| 15 | | PTZ | 100 | 60 |
| | 1.20 | MES | 100 | 30 |
| 16 | | PTZ | 300 | — |
| | 1.40 | MES | 100 | 30 |
| 17 | | PTZ | 300 | — |
| | 1.60 | MES | 100 | 100 |
| 18 | | PTZ | 100 | 80 |
| | 1.57 | MES | 30 | 100 |
| 19 | | PTZ | 100 | 60 |
| 2-benzyl- | | MES | | |
| pyrazolo- | 0.40 | PTZ | 100 | 100 |
| [3,4-d]- | | | 100 | — |
| pyrimidine | | | | |
| Controls | | | | |
| Carbamazepine | | MES | 100 | 100 |
| | | PTZ | 100 | 0 |
| Valproate | | MES | 100 | 0 |
| | | PTZ | 100 | 30 |

Comments for Table 1:
[1] Numbering of these Examples corresponds to the Examples in Tables 2, 3, and 4. In Examples 1–13 X = 0, and in Examples 14–20 X = S. The values of Y are identified in Tables 3 and 4 for each Example.
[2] Octanol/water partition coefficient
[3] Mouse i.p.: MES = maximal electroshock, PTZ = s.c. pentetrazole
[4] In mg/kg
[5] In % of the protected animals; n.t. = not tested 2. Antiallergic/Antiasthmatic Activity The compounds of the present invention were tested in vivo for antiasthmatic action after oral administration to male guinea-pigs, and the inhibition of the infiltration of the eosinophilic granulocytes into the lungs was determined. Male guinea-pigs (Dunkin Hartley Shoe) weighing 200–250 g were actively sensitized by an s.c. injection of ovalbumin (10 μg+1 mg of aluminum hydroxide) and boosted 2 weeks later. One week after boosting with ovalbumin, the animals were challenged with an aerosol of 0.5% strength ovalbumin solution for 20–30 sec. 24 hours later, a bronchoalveolar lavage (BAL) was carried out in the animals under urethane anaesthesia using 2×5 ml of saline solution. The lavage fluid was collected and centrifuged at 400×g for 10 min and the cell pellets were suspended in 1 ml of saline solution. The eosinophilic granulocytes were counted microscopically in a Neubauer chamber. A Becton Dickinson test kit (No. 5877) for eosinophils was used for staining. The test kit used phloxine B as a selective stain for eosinophils. The eosinophils in the BAL were counted for each animal and the eosinophils were calculated in millions/animal. The test substances were administered orally 2 hours before allergen challenge.

The percentage inhibition of eosinophilia of the group treated with substance is calculated according to the following formula:

$(A-C)-(B-C)/(A-C)\times 100 = \%$ inhibition

A=eosinophils in the untreated challenge control group
B=eosinophils in the challenge group treated with substance C=eosinophils in the unchallenged control group For example, the compound of Example 3 at a dose of 100 mg/kg inhibits the infiltration of the eosinophilic granulocytes into the lung, which is characteristic of bronchial asthma, by 74%.

The compounds of the present invention are suitable, for example, for the treatment of bronchial asthma, rhinoconjunctivitis and atopic dermatitis.

The compounds according to the invention bind subtype-specifically (A3) to the adenosine receptor. Adenosine A3 receptor antagonists can prevent mediator secretion by the blockage of their receptors. Recently, it has been shown that adenosine A3 receptor antagonists prevent the lowering of the intracellular cAMP concentration even in the eosinophilic granulocytes and thereby also the release of the cytokines and other mediators from these cells (Jacobson et al., 1995). As a result, on the one hand the unpleasant, acute symptoms severely impairing quality of life can be alleviated and on the other hand the inflammatory processes underlying the disease can also be suppressed.

TABLE 2

Ki values [$\mu$M] at the adenosine receptor (A3) and selectivities

| Example[1] | $K_i$ values [$\mu$M] | $A_3/A_1$ | $A_3/A_2$ |
| --- | --- | --- | --- |
| 1 | 3.2 | 0.7 | 0.01 |
| 2 | 2 | 0.02 | 0.06 |
| 3 | 0.43 | 0.008 | 0.005 |
| 4 | 0.49 | 0.008 | <0.0005 |
| 5 | 0.79 | 0.002 | 0.007 |
| 6 | 4 | 0.01 | 0.08 |
| 9 | 1 | 0.002 | 0.004 |
| 10 | 1.6 | 0.02 | 0.02 |
| 11 | 0.71 | 0.04 | 0.01 |
| 12 | 9.8 | 0.5 | 0.01 |
| 13 | 8.3 | 0.4 | 0.02 |
| 15 | 0.5 | 0.007 | <0.001 |
| 16 | 0.34 | 0.005 | <0.001 |
| 17 | 0.5 | 0.008 | <0.001 |

Comments for Table 2:
[1] Numbering of the Examples corresponds to the Examples in Tables 1, 3 and 4

The Ki values shown in Table 2 demonstrate that the compounds of the present invention bind to the receptors which show selectivity values (columns 2 and 3) that selectively bind these compounds. A biological activity can possibly be mediated by means of this novel binding mechanism.

The following examples further illustrate the invention.

General procedure for the preparation of compounds of Formula (1) and their tautomers where X is oxygen as shown in Table 3, Examples 1–13.

30 mmol of compound of Formula (2) are added to 40 ml formamide and the mixture is heated at between 100 and 200° C. for 8–16 hours. After cooling, the precipitated crude product is filtered off with suction and a recrystallization (RC) is carried out using a suitable solvent, e.g. ethanol or DMF.

TABLE 3

Pyrazolo[3,4-d]pyrimidines, where X = O

| Example | Y | Yield [%] | M.p. (° C.) | Recrystallization from: |
| --- | --- | --- | --- | --- |
| 1 | 2-F | 40 | 230–234 | EtOH |
| 2 | 2-Cl | 51 | 228–231 | EtOH |

TABLE 3-continued

Pyrazolo[3,4-d]pyrimidines, where X = O

| Example | Y | Yield [%] | M.p. (° C.) | Recrystallization from: |
| --- | --- | --- | --- | --- |
| 3 | 2-Br | 26 | 227–232 | EtOH |
| 4 | 2-I | 28 | 265–268 | EtOH |
| 5 | 2-CF$_3$ | 48 | 224–226 | EtOH |
| 6 | 2-CH$_3$ | 65 | 262–264 | EtOH |
| 7 | 3-CF$_3$ | 56 | 243–244 | EtOH |
| 8 | 2,6-F$_2$ | 42 | 251–253 | EtOH |
| 9 | 2-Cl-6-F | 61 | 254–256 | EtOH |
| 10 | 2,6-Cl$_2$ | 76 | 268–271 | EtOH |
| 11 | 2,4-Cl$_2$ | 41 | 255–257 | EtOH |
| 12 | 4-OCH$_3$ | 64 | 260–261 | EtOH |
| 13 | 2-Cl-4,5-OCH$_2$O | 42 | 258–260 | DMF |

General procedure for the preparation of the compounds of Formula (1) and their tautomers where X is sulfur as shown in Table 4.

Method A 20 mmol of the compound of Formula (1) where X is oxygen and 80 mmol of phosphorus pentasulfide are added to 100 ml of pyridine and the mixture is heated at between 80 and 115° C. for 4 to 8 hours. After cooling, the precipitated crude product is purified from a suitable solvent, suitably ethanol, by recrystallization (RC).

Method B 10 mmol of the compound of Formula (1) where X is oxygen and 20 mmol of 2,4-bis(4-methoxyphenyl)-1,3-dithia-2,4-diphosphetane-2,4-disulfide are added to 100 ml xylene and the mixture is heated for 8 to 24 hours. The crude product is filtered off and purified as in Method A.

TABLE 4

Pyrazolo[3,4-d]pyrimidines, where X = S

| Example | Y | Yield [%] | M.p. (° C.) | Method | Recrystallization from |
| --- | --- | --- | --- | --- | --- |
| 14 | 2-F | 62 | 272–275 | A | EtOH |
| 15 | 2-Cl | 98 | 247–249 | B | DMF |
| 16 | 2-Br | 66 | 263–264 | A | EtOH |
| 17 | 2-I | 64 | 278–281 | A | DMF |
| 18 | 2-CF$_3$ | 93 | 303–305 | B | EtOH |
| 19 | 2,6-F$_2$ | 72 | 293–297 | B | EtOH |
| 20 | 2-Cl-6-F | 47 | 252–253 | A | AcOH |

We claim:

1. A compound of Formula (1)

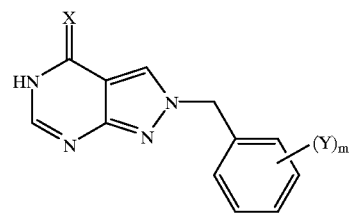

(1)

their tautomers, and their pharmaceutically acceptable salts, wherein

X is oxygen or sulfur and

Y is halogen, $C_{1-4}$-alkyl, $C_{1-4}$-alkoxy, trifluoromethyl m is 1 or 2 or trifluoromethoxy.

2. Compounds of Formula (1) of claim 1, being:

2-(2-fluorobenzyl)pyrazolo[3,4-d]pyrimidin-4(5H)-one,
2-(2-chlorobenzyl)pyrazolo[3,4-d]pyrimidin-4(5H)-one,
2-(2-bromobenzyl)pyrazolo[3,4-d]pyrimidin-4(5H)-one,
2-(2-iodobenzyl)pyrazolo[3,4-d]pyrimidin-4(5H)-one,
2-(2-trifluoromethylbenzyl)pyrazolo[3,4-d]pyrimidin-4(5H)-one,
2-(2-methylbenzyl)pyrazolo[3,4-d]pyrimidin-4(5H)-one,
2-(3-trifluoromethylbenzyl)pyrazolo[3,4-d]pyrimidin-4(5H)-one,
2-(2,-difluorobenzyl)pyrazolo[3,4-d]pyrimidin-4(5H)-one,
2-(2-chloro-6-fluorobenzyl)pyrazolo[3,4-d]pyrimidin-4(5H)-one,
2-(2,6-dichlorobenzyl)pyrazolo[3,4-d]pyrimidin-4(5H)-one,
2-(2,4-dichloroben zyl)pyrazolo[3,4-d]pyrimidin-4(5H)-one,
2-(4-methoxybenzyl)pyrazolo[3,4-d]pyrimidin-4(5H)-one,
2-(2-chloro-4,5-methylenedioxybenzyl)pyrazolo[3,4-d]pyrimidin-4(5H)-one,
2-(2-chlorobenzyl)pyrazolo[3,4-d]pyrimidine-4(5H)-thione,
2-(2-bromobenzyl)pyrazolo[3,4-d]pyrimidine-4(5H)-thione,
2-(2-iodobenzyl)pyrazolo[3,4-d]pyrimidine-4(5H)-thione,
2-(2-trifluoromethylbenzyl)pyrazolo[3,4-d]pyrimidine-4(5H)-thione, and,
2-(2,6-difluorobenzyl)pyrazolo[3,4-d]pyrimidine-4(5H)-thione.

3. A process for the preparation of pyrazolo[3,4-d]pyrimidines of claim 1 where X is oxygen, which comprises cyclizing with an alkyl orthoformate, a mixture of formic acid and acetic anhydride, or a formamide a compound of Formula (2),

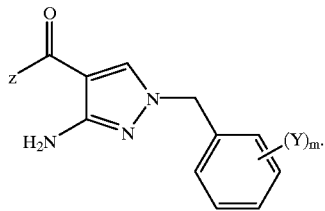

(2)

wherein Z is hydroxyl, alkoxy or amino m is 1 or 2.

4. The process of claim 3, wherein at least one 3-aminopyrazole-4-carboxamide of Formula (2) is cyclized with at least one of an alkyl orthoformate and a mixture of formic acid and acetic anhydride.

5. The process for the preparation of the compound of claim 1 where X is sulfur, which comprises reacting a compound of Formula (1) where X is oxygen with phosphorus pentasulfide, or 2,4-bis(4-methoxyphenyl)-1,3-dithia-2,4-diphosphetane-2,4-disulfide.

6. A pharmaceutical composition which comprises at least one pyrazolo-[3,4-d]pyrimidines of claim 1 or its pharmaceutically acceptable salt as active compound, and one or more pharmaceutically acceptable auxiliary and excipient, and optionally a diluent.

7. A pharmaceutical composition comprising at least one compound of claim 2, or its pharmaceutically acceptable salt as active compound, and one or more pharmaceutically acceptable auxiliary and excipient and, optionally a diluent.

8. A process for treating an epileptic condition, which comprises administering to a patient in need therefor an effective amount of a compound of claim 1.

9. A process for treating an allergic/asthmatic disease, which comprises advertising to a patient an effective amount of a compound of claim 1.

* * * * *